United States Patent
Penna

(10) Patent No.: US 10,342,528 B2
(45) Date of Patent: Jul. 9, 2019

(54) SURGICAL SUTURING INSTRUMENT

(71) Applicant: Covidien LP, Mansfield, MA (US)

(72) Inventor: Christopher Penna, Guilford, CT (US)

(73) Assignee: Covidien LP, Mansfield, MA (US)

( * ) Notice: Subject to any disclaimer, the term of this patent is extended or adjusted under 35 U.S.C. 154(b) by 151 days.

(21) Appl. No.: 15/471,117

(22) Filed: Mar. 28, 2017

(65) Prior Publication Data
US 2017/0196550 A1    Jul. 13, 2017

Related U.S. Application Data

(62) Division of application No. 14/624,886, filed on Feb. 18, 2015, now Pat. No. 9,636,103.
(Continued)

(51) Int. Cl.
*A61B 17/04* (2006.01)
*A61B 90/00* (2016.01)
(Continued)

(52) U.S. Cl.
CPC ...... *A61B 17/0469* (2013.01); *A61B 17/0467* (2013.01); *A61B 17/0482* (2013.01); *A61B 17/0491* (2013.01); *A61B 90/08* (2016.02); *A61B 17/295* (2013.01); *A61B 2017/00353* (2013.01); *A61B 2017/0472* (2013.01);
(Continued)

(58) Field of Classification Search
CPC ............ A61B 17/0467; A61B 17/0491; A61B 17/0469; A61B 90/08; A61B 17/0482; A61B 17/295; A61B 2017/0472; A61B 2017/06042; A61B 2017/2931;
(Continued)

(56) References Cited

U.S. PATENT DOCUMENTS 1,822,330 A    9/1931  Ainslie
2,327,353 A    8/1943  Karle
(Continued)

FOREIGN PATENT DOCUMENTS

CN    203564286 U    4/2014
EP    169044 A2    1/1986
GB    2337934 A    12/1999

OTHER PUBLICATIONS

International Search Report for PCT/US07/021495 date of completion is Mar. 19, 2008 (2 pages).
(Continued)

*Primary Examiner* — Phong Son H Dang

(57) ABSTRACT

A surgical suturing instrument includes a handle assembly, an elongate member extending distally from the handle assembly, and an end effector attached to the distal end of the elongate member. The end effector may include a first jaw member movable relative to a second jaw member between an open position and an approximated position for grasping tissue. Each of the jaw members defines a knife slot, a first needle slot, and a second needle slot extending along a longitudinal axis of the end effector. The end effector also includes a knife assembly and an upper assembly pivotably coupled to an upper knife flange of the knife assembly. The upper assembly includes an upper bellcrank, a first needle, a first suture passing through a first aperture defined by the first needle, a second needle, and a second suture passing through a second aperture defined by the second needle.

9 Claims, 11 Drawing Sheets

Related U.S. Application Data

(60) Provisional application No. 62/042,844, filed on Aug. 28, 2014.

(51) Int. Cl.
  *A61B 17/295* (2006.01)
  *A61B 17/00* (2006.01)
  *A61B 17/06* (2006.01)
  *A61B 17/29* (2006.01)
  *A61B 17/32* (2006.01)

(52) U.S. Cl.
  CPC .............. *A61B 2017/06019* (2013.01); *A61B 2017/06042* (2013.01); *A61B 2017/06176* (2013.01); *A61B 2017/2931* (2013.01); *A61B 2017/320052* (2013.01)

(58) Field of Classification Search
  CPC ......... A61B 2017/320052; A61B 2017/00353; A61B 2017/06019
  See application file for complete search history.

(56) References Cited

U.S. PATENT DOCUMENTS

| | | |
|---|---|---|
| 3,073,311 A | 1/1963 | Tibbs et al. |
| 3,842,840 A | 10/1974 | Schweizer |
| 4,236,470 A | 12/1980 | Stenson |
| 5,037,433 A | 8/1991 | Wilk et al. |
| 5,042,707 A | 8/1991 | Taheri |
| 5,100,430 A | 3/1992 | Avellanet et al. |
| 5,209,747 A | 5/1993 | Knoepfler |
| 5,282,832 A | 2/1994 | Toso et al. |
| 5,300,082 A | 4/1994 | Sharpe et al. |
| 5,308,353 A | 5/1994 | Beurrier |
| 5,314,445 A | 5/1994 | Heidmueller nee Degwitz et al. |
| 5,330,502 A | 7/1994 | Hassler et al. |
| 5,350,391 A | 9/1994 | Iacovelli |
| 5,374,277 A | 12/1994 | Hassler |
| 5,389,103 A | 2/1995 | Melzer et al. |
| 5,403,342 A | 4/1995 | Tovey et al. |
| 5,439,478 A | 8/1995 | Palmer |
| 5,454,822 A | 10/1995 | Schob et al. |
| 5,454,823 A | 10/1995 | Richardson et al. |
| 5,454,827 A | 10/1995 | Aust et al. |
| 5,480,406 A | 1/1996 | Nolan et al. |
| 5,540,706 A | 7/1996 | Aust et al. |
| 5,564,615 A | 10/1996 | Bishop et al. |
| 5,575,799 A | 11/1996 | Bolanos et al. |
| 5,582,617 A | 12/1996 | Klieman et al. |
| 5,591,181 A | 1/1997 | Stone et al. |
| 5,601,224 A | 2/1997 | Bishop et al. |
| 5,620,415 A | 4/1997 | Lucey et al. |
| 5,630,824 A | 5/1997 | Hart |
| 5,645,553 A | 7/1997 | Kolesa et al. |
| 5,674,229 A | 10/1997 | Tovey et al. |
| 5,690,652 A | 11/1997 | Wurster et al. |
| 5,690,653 A | 11/1997 | Richardson et al. |
| 5,725,556 A | 3/1998 | Moser et al. |
| 5,735,877 A | 4/1998 | Pagedas |
| 5,752,973 A | 5/1998 | Kieturakis |
| 5,759,188 A | 6/1998 | Yoon |
| 5,766,196 A | 6/1998 | Griffiths |
| 5,779,646 A | 7/1998 | Koblish et al. |
| 5,792,165 A | 8/1998 | Klieman et al. |
| 5,797,537 A | 8/1998 | Oberlin et al. |
| 5,797,927 A | 8/1998 | Yoon |
| 5,814,054 A | 9/1998 | Kortenbach et al. |
| 5,817,119 A | 10/1998 | Klieman et al. |
| 5,827,323 A | 10/1998 | Klieman et al. |
| 5,843,126 A | 12/1998 | Jameel |
| 5,876,412 A | 3/1999 | Piraka |
| 5,895,393 A | 4/1999 | Pagedas |
| 5,897,563 A | 4/1999 | Yoon et al. |
| 5,906,630 A | 5/1999 | Anderhub et al. |
| 5,928,136 A | 7/1999 | Barry |
| 5,938,668 A | 8/1999 | Scirica et al. |
| 5,954,731 A | 9/1999 | Yoon |
| 5,954,733 A | 9/1999 | Yoon |
| 5,957,937 A | 9/1999 | Yoon |
| 5,984,932 A | 11/1999 | Yoon |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,015,428 A | 1/2000 | Pagedas |
| 6,017,358 A | 1/2000 | Yoon et al. |
| 6,027,522 A | 2/2000 | Palmer |
| 6,066,160 A | 5/2000 | Colvin et al. |
| 6,077,287 A | 6/2000 | Taylor et al. |
| 6,080,180 A | 6/2000 | Yoon et al. |
| 6,086,601 A | 7/2000 | Yoon |
| 6,086,608 A | 7/2000 | Ek et al. |
| 6,126,665 A | 10/2000 | Yoon |
| 6,139,563 A | 10/2000 | Cosgrove, III et al. |
| 6,143,005 A | 11/2000 | Yoon et al. |
| 6,171,316 B1 | 1/2001 | Kovac et al. |
| 6,206,893 B1 | 3/2001 | Klein et al. |
| 6,214,028 B1 | 4/2001 | Yoon et al. |
| 6,223,100 B1 | 4/2001 | Green |
| 6,224,614 B1 | 5/2001 | Yoon |
| 6,261,307 B1 | 7/2001 | Yoon et al. |
| 6,263,558 B1 | 7/2001 | Blanch et al. |
| 6,319,262 B1 | 11/2001 | Bates et al. |
| 6,358,259 B1 | 3/2002 | Swain et al. |
| 6,494,888 B1 | 12/2002 | Laufer et al. |
| 6,506,196 B1 | 1/2003 | Laufer |
| 6,517,539 B1 | 2/2003 | Smith et al. |
| 6,569,105 B1 | 5/2003 | Kortenbach et al. |
| 6,582,450 B2 | 6/2003 | Ouchi |
| 6,599,310 B2 | 7/2003 | Leung et al. |
| 6,638,287 B2 | 10/2003 | Danitz et al. |
| 6,663,639 B1 | 12/2003 | Laufer et al. |
| 6,663,641 B1 | 12/2003 | Kovac et al. |
| 6,666,854 B1 | 12/2003 | Lange |
| 6,676,676 B2 | 1/2004 | Danitz et al. |
| 6,743,239 B1 | 6/2004 | Kuehn et al. |
| 6,743,240 B2 | 6/2004 | Smith et al. |
| 6,755,843 B2 | 6/2004 | Chung et al. |
| 6,773,441 B1 | 8/2004 | Laufer et al. |
| 6,821,285 B2 | 11/2004 | Laufer et al. |
| 6,835,200 B2 | 12/2004 | Laufer et al. |
| 6,889,116 B2 | 5/2005 | Jinno |
| 6,936,061 B2 | 8/2005 | Sasaki |
| 6,972,017 B2 | 12/2005 | Smith et al. |
| 6,981,628 B2 | 1/2006 | Wales |
| 6,997,931 B2 | 2/2006 | Sauer et al. |
| 7,052,489 B2 | 5/2006 | Griego et al. |
| 7,063,715 B2 | 6/2006 | Onuki et al. |
| 7,094,251 B2 | 8/2006 | Bonutti et al. |
| 7,107,124 B2 | 9/2006 | Green |
| 7,153,314 B2 | 12/2006 | Laufer et al. |
| 7,166,116 B2 | 1/2007 | Lizardi et al. |
| 7,248,944 B2 | 7/2007 | Green |
| 7,625,387 B2 | 12/2009 | Wixey et al. |
| 7,879,046 B2 | 2/2011 | Weinert et al. |
| 8,177,794 B2 | 5/2012 | Cabrera et al. |
| 8,313,509 B2 | 11/2012 | Kostrzewski |
| 9,636,103 B2 | 5/2017 | Penna |
| 2002/0072702 A1 | 6/2002 | Quay |
| 2002/0147456 A1 | 10/2002 | Diduch et al. |
| 2003/0065336 A1 | 4/2003 | Xiao |
| 2003/0105476 A1 | 6/2003 | Sancoff et al. |
| 2003/0116670 A1 | 6/2003 | Gentry |
| 2003/0233106 A1 | 12/2003 | Dreyfuss |
| 2004/0133238 A1 | 7/2004 | Cerier |
| 2005/0096694 A1 | 5/2005 | Lee |
| 2006/0229671 A1 | 10/2006 | Steiner et al. |
| 2006/0253126 A1 | 11/2006 | Bjerken et al. |
| 2006/0282093 A1 | 12/2006 | Shelton et al. |
| 2007/0010832 A1 | 1/2007 | Manzo |
| 2007/0250118 A1 | 10/2007 | Masini |
| 2007/0270885 A1 | 11/2007 | Weinert et al. |

(56) References Cited

U.S. PATENT DOCUMENTS

| | | | |
|---|---|---|---|
| 2008/0147116 A1* | 6/2008 | Smith ................ | A61B 17/0643 |
| | | | 606/220 |
| 2009/0281563 A1 | 11/2009 | Newell et al. | |
| 2010/0010512 A1* | 1/2010 | Taylor .................... | A61B 17/04 |
| | | | 606/144 |
| 2011/0118760 A1 | 5/2011 | Gregoire et al. | |
| 2011/0178536 A1* | 7/2011 | Kostrzewski ...... | A61B 17/0401 |
| | | | 606/144 |

OTHER PUBLICATIONS

European Search Report for EP 11250054.1-1269 date of completion is Jun. 17, 2011 (4 pages).
Extended European Search Report from Appl. No. EP 15182634.4 dated Feb. 18, 2016.
Chinese Office Action issued in Appl. No. CN 201510536655.5 dated Dec. 3, 2018, together with English language translation (15 pages).

\* cited by examiner

SURGICAL SUTURING INSTRUMENT

CROSS-REFERENCE TO RELATED APPLICATIONS

This application is a divisional application of U.S. patent application Ser. No. 14/624,886, filed on Feb. 18, 2015, which claims the benefit of and priority to U.S. Provisional Patent Application No. 62/042,844, filed Aug. 28, 2014, the entire disclosure of each of which is incorporated by reference herein.

BACKGROUND

1. Technical Field

The present disclosure relates to instruments, systems, and methods for suturing or stitching and, more particularly, to end effectors, systems, and methods for surgical suturing and/or stitching through an access device.

2. Discussion of Related Art

In many surgical procedures, including those involved in minimally invasive surgery and those in non-minimally invasive procedures, suturing bodily organs or tissue may be part of the procedure. Minimally invasive suturing procedures can be challenging due to the small openings through which the suturing of bodily organs or tissues must be accomplished.

During open surgery, suturing of bodily organs or tissue is achieved through the use of a sharp needle having a length of suture material attached at one of its ends. The surgeon stitches tissue by penetrating a suture needle through bodily tissue and pulling the suture material through the bodily tissue. Once the suture material is pulled through the bodily tissue, the surgeon forms a knot in the suture material to secure the suture material to the bodily tissue.

During endoscopic surgery, knotting of the suture material is especially time consuming and burdensome due to the difficulty in maneuvering a suture needle through the small endoscopic openings.

Many attempts have been made to provide devices to overcome the disadvantages of conventional suturing. Such devices include clip appliers, clamping devices and stapling devices. However, such prior devices are limiting in that these devices dispense staples, clips, clamps, or other fasteners which are of a predetermined length, and are not able to adapt or adjust to different tissue thicknesses.

SUMMARY

In an aspect of the present disclosure, an end effector for use with a surgical instrument is disclosed. The end effector includes a first jaw member movable relative to a second jaw member between an open position and an approximated position for grasping tissue. Each of the jaw members defines a knife slot, a first needle slot, and a second needle slot extending along a longitudinal axis of the end effector. The first needle slot and the second needle slot may be located on opposite sides of the knife slot. The end effector also includes a knife assembly and an upper assembly pivotably coupled to an upper knife flange of the knife assembly. The upper assembly includes an upper bellcrank, a first needle, a first suture passing through a first aperture defined by the first needle, a second needle, and a second suture passing through a second aperture defined by the second needle.

In an embodiment, the end effector further includes a first upper cam surface and a second upper cam surface extending along a length of the first jaw member, and a first cam follower and a second cam follower disposed on the upper bellcrank. The first and second cam followers are configured to slide along the first upper cam surface and the second upper cam surface, respectively. Any of the cam surfaces may be undulating or wavelike surfaces.

In an embodiment, the end effector further includes a lower assembly. The lower assembly may include a first lower bellcrank, a second lower bellcrank, a ferrule, and a third suture coupled to the ferrule. Each of the first lower bellcrank and a second lower bellcrank is pivotably coupled to the lower knife flange about respective pivot points. Each of the first lower bellcrank and the second lower bellcrank may have a proximal lip, a distal lip, and a cam follower. The ferrule may have a proximal waist configured to engage the proximal lip of the first lower bellcrank and the proximal lip of the second lower bellcrank, and a distal waist configured to engage the distal lip of the first lower bellcrank and the distal lip of the second lower bellcrank.

In an embodiment, the end effector further includes a first lower cam channel and a second lower cam channel extending along a length of the second jaw member. The cam follower of the first lower bellcrank is configured to slide along the first lower cam channel and the cam follower of the second lower bellcrank is configured to slide along the second lower cam channel.

In another aspect of the present disclosure, a surgical suturing instrument is disclosed including a handle assembly, an elongate member extending distally from the handle assembly and an end effector attached to the distal end of the elongate member. The end effector includes a first jaw member movable relative to a second jaw member between an open position and an approximated position for grasping tissue. Each of the jaw members defines a knife slot and may further define a first needle slot, and a second needle slot extending along a longitudinal axis of the end effector. The first needle slot and the second needle slot may be located on opposite sides of the knife slot. The end effector also includes a knife assembly and an upper bellcrank pivotably coupled to an upper knife flange of the knife assembly. A first needle may be pivotably coupled to the upper bellcrank with a first suture passing through a first aperture defined by the first needle. A second needle may be pivotably coupled to the upper bellcrank with a second suture passing through a second aperture defined by the second needle.

In an embodiment, the handle assembly may include a fixed handle and a movable handle. Movement of the movable handle toward the fixed handle may cause approximation of the first jaw member relative to the second jaw member and movement of the movable handle toward the fixed handle may cause approximation of the first jaw member relative to the second jaw member and distal advancement of the knife assembly through the end effector.

In an embodiment, the end effector further includes a first upper cam surface and a second upper cam surface extending along a length of the first jaw member, and a first cam follower and a second cam follower disposed on the upper bellcrank. The first and second cam followers are configured to slide along the first upper cam surface and the second upper cam surface, respectively. Any of the cam surfaces may be undulating or wavelike surfaces.

In an embodiment, the end effector further includes a lower assembly. The lower assembly may include a first lower bellcrank, a second lower bellcrank, a ferrule, and a third suture coupled to the ferrule. Each of the first lower bellcrank and a second lower bellcrank are pivotably coupled to the lower knife flange about respective pivot points. Each of the first lower bellcrank and the second lower bellcrank may have a proximal lip, a distal lip, and a cam follower. The ferrule may have a proximal waist configured to engage the proximal lip of the first lower bellcrank and the proximal lip of the second lower bellcrank, and a distal waist configured to engage the distal lip of the first lower bellcrank and the distal lip of the second lower bellcrank.

In an embodiment, the end effector further includes first lower cam channel and a second lower cam channel extending along a length of the second jaw member. The cam follower of the first lower bellcrank is configured to slide along the first lower cam channel and the cam follower of the second lower bellcrank is configured to slide along the second lower cam channel.

In a further aspect, a surgical suturing instrument includes an upper jaw member and a lower jaw member, an upper reciprocating assembly associated with the upper jaw member, and a lower advancing assembly associated with the lower jaw member, wherein the upper reciprocating assembly has a pair of needles and a suture carried by each one of the pair of needles, the lower advancing assembly having a pair of ferrules and a suture associated with each of the pair of ferrules, the lower advancing assembly being movable to advance each suture of the lower advancing assembly.

In the surgical suturing instrument, the upper jaw member can have a cam assembly for moving the upper reciprocating assembly through reciprocating movement. The lower jaw member can have a cam assembly for moving the lower advancing assembly through the lower jaw member.

The upper jaw member and/or the lower jaw member can have a pair of longitudinal needle slots. The upper jaw member and the lower jaw member can each have a knife slot.

A knife assembly is arranged to move through the knife slots of the upper jaw member and the lower jaw member, the knife assembly having a blade for cutting tissue.

The knife assembly can have an upper portion for engaging the upper jaw member and a lower portion for engaging the lower jaw member, the knife assembly maintaining the approximated position of the upper jaw member and lower jaw member.

The upper reciprocating assembly may pass the pair of needles into the lower jaw member, and the lower advancing assembly may pass the pair of ferrules through the lower jaw member. The sutures of the upper jaw member form loops and the sutures of the lower jaw member are passed through the loops to effect stitching of any tissue disposed between the upper jaw member and the lower jaw member.

Further, to the extent consistent, any of the aspects and/or embodiments described herein may be used in conjunction with any or all of the other aspects and/or embodiments described herein.

BRIEF DESCRIPTION OF THE DRAWINGS

Various aspects and embodiments of the present disclosure are described hereinbelow with reference to the drawings, wherein.

DETAILED DESCRIPTION

Figure 1:
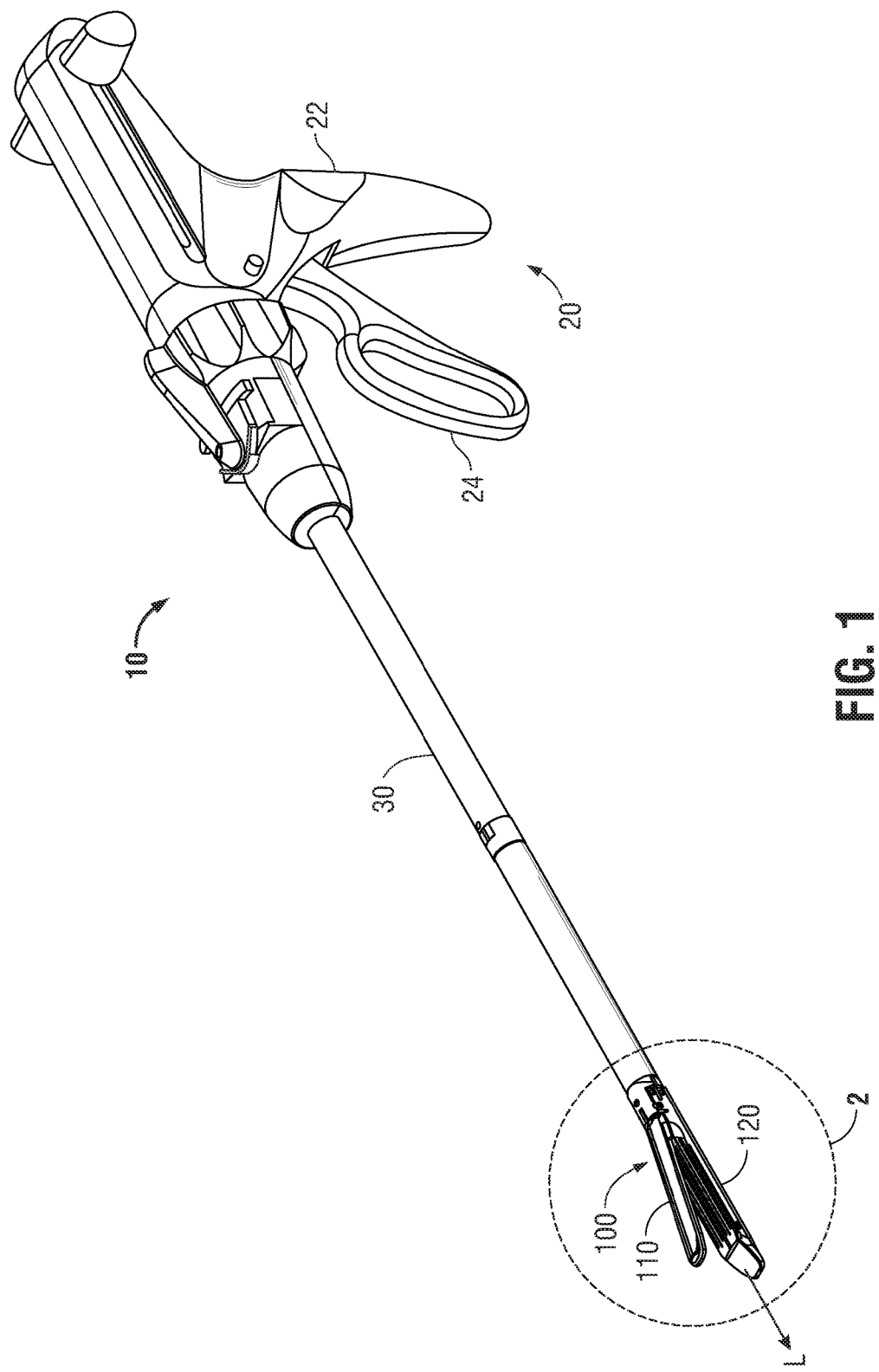
FIG. 1 is a perspective view of an embodiment of a surgical suturing instrument in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Details of various embodiments of surgical suturing instruments in accordance with the present disclosure will now be described in detail.

Referring now in specific detail to the drawings, in which like reference numbers identify similar or identical elements, FIG. 1 illustrates a surgical suturing instrument 10. Surgical suturing instrument 10 includes a handle assembly 20 including a fixed handle 22, and a movable handle 24. The movable handle 24 is movable towards the fixed handle 22 to actuate the instrument 10. A suitable handle assembly is described in U.S. Pat. No. 5,865,361, which is incorporated herein in its entirety by reference. An elongate tubular body portion 30 extends distally from handle assembly 20 and defines a longitudinal axis "L" that extends through proximal and distal end portions of elongate tubular body portion 30. An end effector 100 is supported on the distal end portion of elongate tubular body portion 30 and is remotely operable by handle assembly 20. Alternately, the body portion 30 can be supported on a robotic arm and actuated by motorized actuator. End effector 100 is adapted to be particularly useful in endoscopic or laparoscopic procedures wherein an endoscopic portion of the stitching device, i.e., end effector 100, is insertable into a surgical site, via an access device (e.g., cannula) (not shown) or the like. Alternately, the end effector 100 is easily adapted for use in a suturing device configured for open surgical procedures as will be discussed in further detail below.

Figure 2:
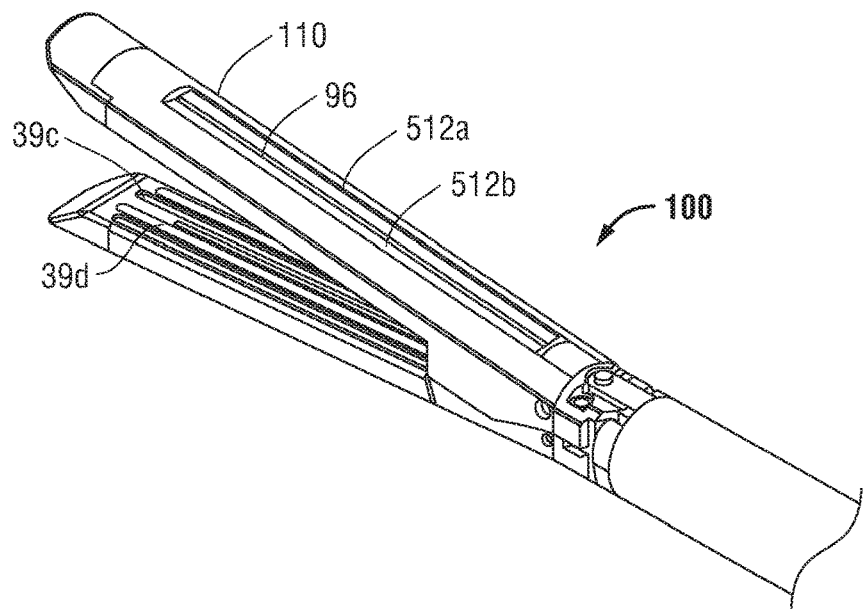
FIG. 2 is an enlarged view of the area of detail in FIG. 1.
Figure 3:
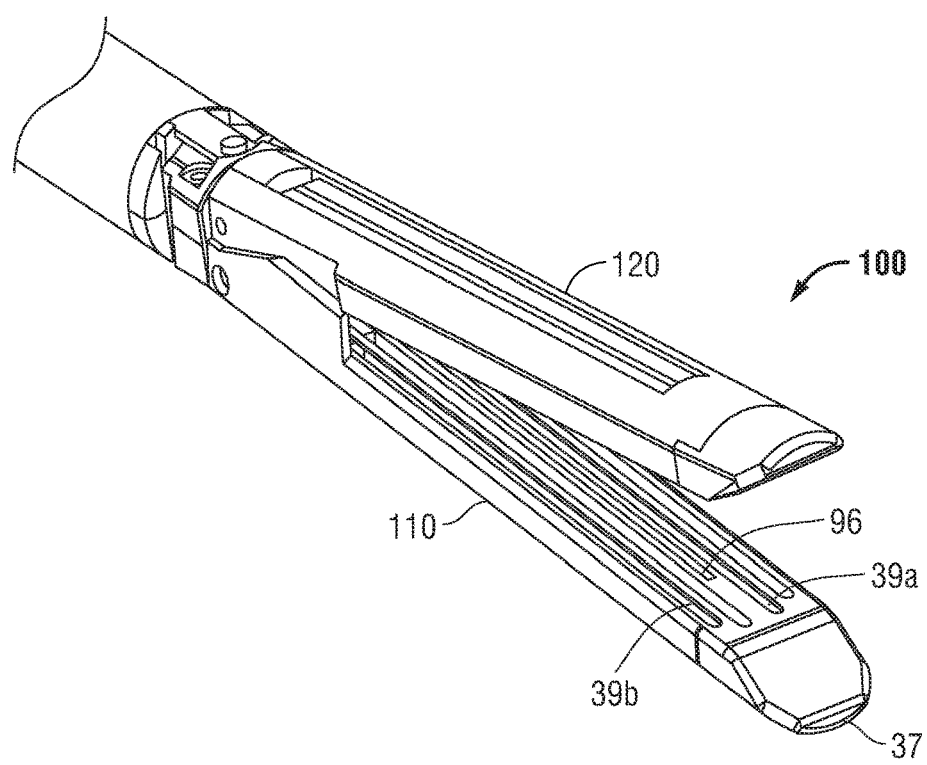
FIG. 3 is a bottom perspective view of the end effector of the surgical suturing instrument shown in FIG. 2.
Figure 9A:
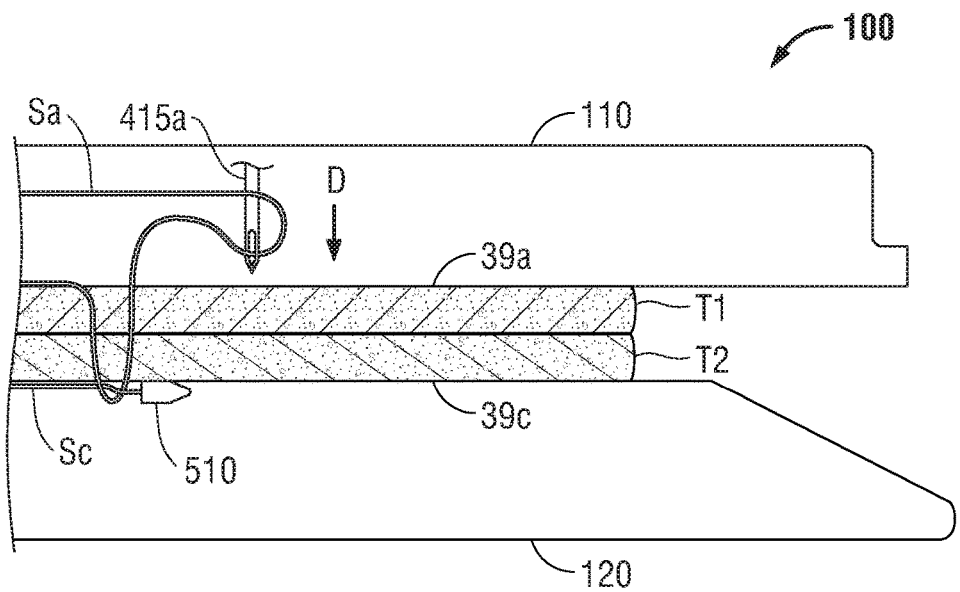
FIG. 9A is a side cross-sectional view of an end effector suturing tissue portions with a needle assembly in a first position.

With reference to FIGS. 2 and 3, end effector 100 includes a first jaw member 110 and a second jaw member 120 movable relative to one another between an open configuration (FIG. 2) and a closed or clamped configuration (FIG. 9A). In embodiments, each of the jaw members 110, 120 defines an opposing longitudinal knife slot 96 which extends along a centerline of the respective jaw member 110, 120. The knife slot 96 extends from a proximal portion of the jaw members 110, 120 to a distal portion of the jaw members 110, 120.

Each of the jaw members 110, 120 further defines longitudinal needle slots 39a-d. In particular, with particular reference to FIG. 3, jaw member 110 defines needle slots 39a and 39b on a surface configured to contact tissue. Additionally, with particular reference to FIG. 2, jaw member 120 defines needle slots 39c and 39d. The needle slots 39a-d are disposed in pairs on either side of the centerline of the jaw members 110, 120. The needle slots 39c and 39d of the lower jaw member 120 oppose the needle slots 39a and 39b of the upper jaw member 110.

Each jaw member 110, 120 may include blunt tip 37 connected to its distal end. The blunt tips 37 assist in atraumatically guiding the end effector 100 between tissue portions and in guiding tissue between the jaw members 110, 120.

Figure 4:
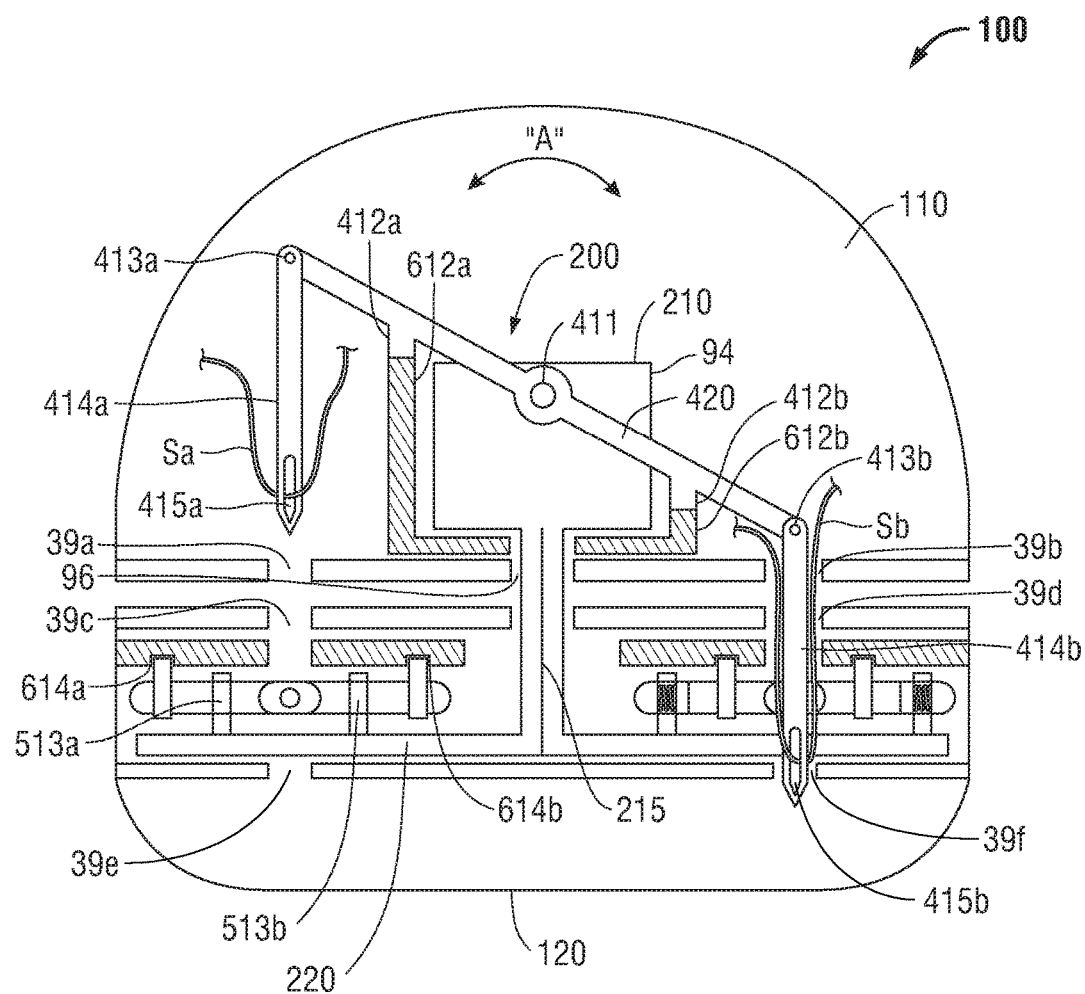
FIG. 4 is a front cross-sectional view of the end effector of the surgical suturing instrument of FIG. 1.
Figure 5:
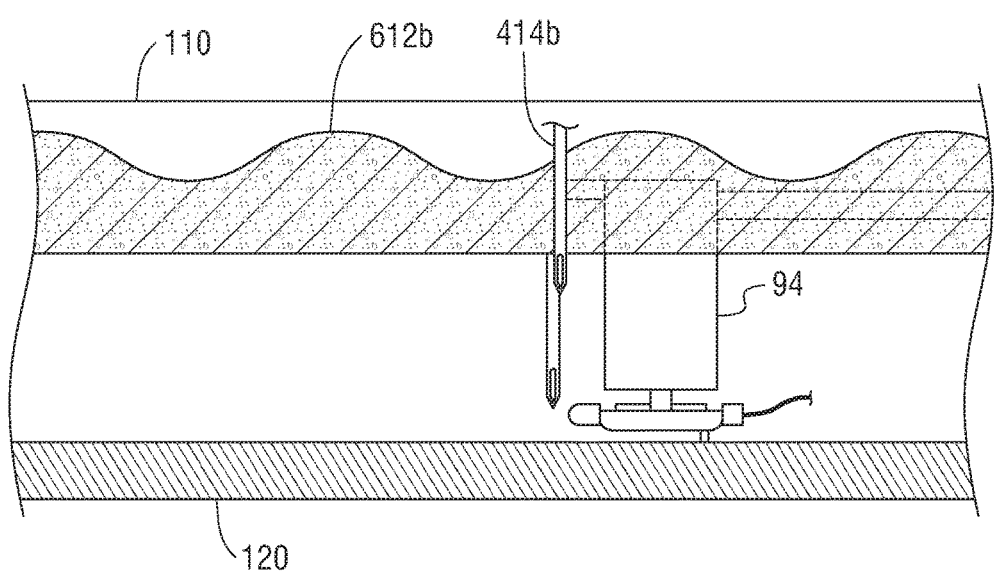
FIG. 5 is a side view of an upper assembly of the surgical suturing instrument shown in FIG. 1.
Figure 6A:
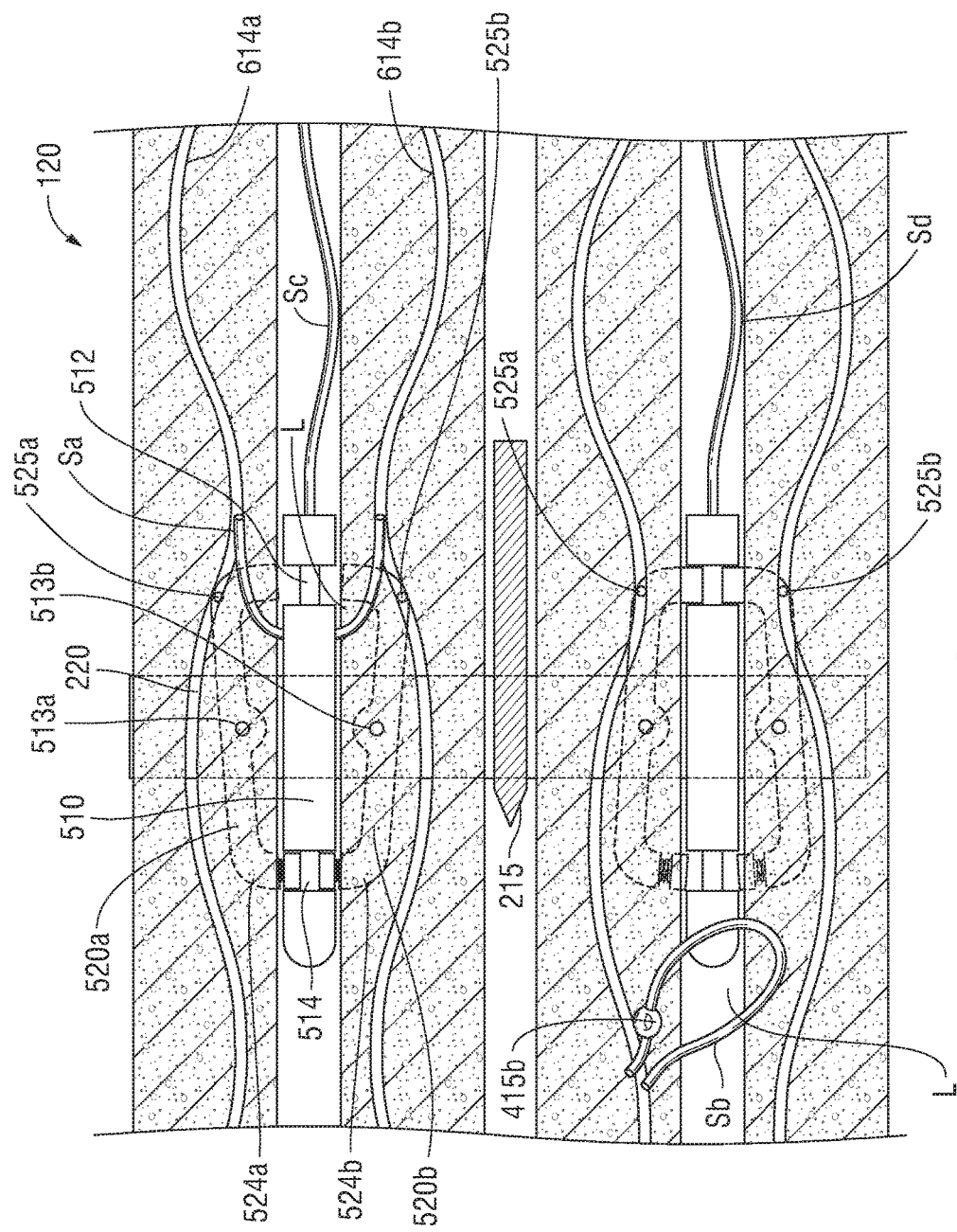
FIG. 6A is a top cross-sectional view of a lower jaw member of the end effector of the surgical suturing instrument of FIG. 1.

Referring briefly to FIGS. 4, 5, and 6A, first jaw member 110 includes upper cam surfaces 612a, 612b (FIG. 4) extending along a length of the first jaw member 110. Upper cam surface 612a is disposed on one side of knife slot 96 and upper cam surface 612b is disposed on the other side of knife slot 96. Additionally, second jaw member 120 includes two sets of lower cam channels 614a, 614b. In embodiments, one set of lower cam channels 614a, 614b is disposed on each side of the knife slot 96. Referring particularly to FIG. 6A, in one embodiment, lower cam channels 614a, 614b have a horizontal sinusoidal configuration. Alternatively, referring to FIG. 6B, lower cam channels 614a, 614b may have a vertical sinusoidal configuration. Upper cam surfaces 612a, 612b and lower cam channels 614a, 614b have a wavelike undulating surface and are configured to impart movement upon upper assembly 400 and lower assembly 500 as the knife assembly 200 is advanced through end effector 100, as will be described in further detail below.

Turning now to FIG. 4, knife assembly 200 includes an upper flange 210, a lower flange 220, and a blade 215 positioned therebetween. Blade 215 is supported on or formed with a vertical strut 215a which interconnects the upper and lower flanges 210, 220. Knife assembly 200 is configured to be advanced distally through end effector 100 upon actuation of handle assembly 20 (FIG. 1) via a drive rod (not shown) extending through elongate tubular body portion 30 (FIG. 1). A more detailed discussion of the distal advancement of the knife assembly 200 through the end effector 100 upon actuation of the handle assembly 20 may be found in U.S. Pat. No. 5,865,361 which has been incorporated herein by reference in its entirety. As knife assembly 200 is advanced through end effector 100, blade 215 travels through knife slot 96 and cuts through tissue that is positioned between jaw members 110, 120.

Figure 7:
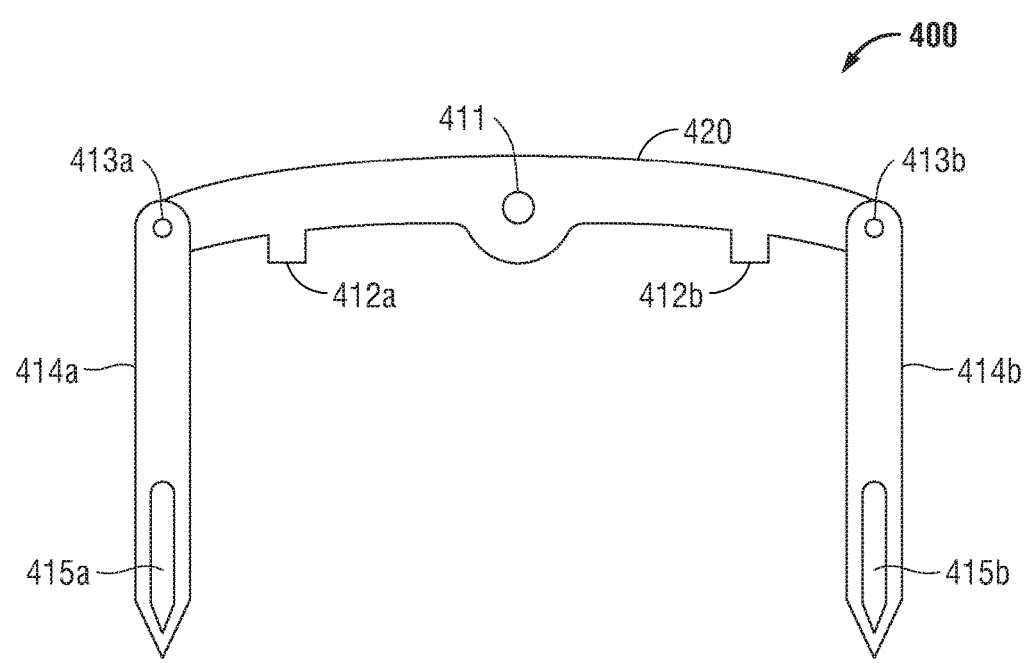
FIG. 7 is a front view of an upper assembly of the surgical suturing instrument of FIG. 1.

With reference also to FIG. 7, the upper assembly 400 includes an upper bellcrank 420 and needles 414a, 414b pivotally coupled to respective ends of the upper bellcrank 420 at pivot points 413a, 413b, respectively. Upper bellcrank 420 includes downwardly extending cam followers 412a, 412b which are configured to engage upper cam surfaces 612a, 612b, of first jaw member 110 respectively (FIG. 4). Although illustrated and described as being on a bottom surface of the upper bellcrank 420, it is envisioned that cam followers 412a, 412b may be located on any portion of the upper assembly 400. Needles 414a, 414b include apertures 415a, 415b, respectively, located on a distal portion thereof. Aperture 415a is configured to receive suture Sa (FIG. 4) and aperture 415b is configured to receive suture Sb. Distal ends of needles 415a, 415b are tapered such that needles 415a, 415b may penetrate through tissue. Additional details with regard to operation of the upper assembly 400 in connection with knife assembly 200 and end effector 100 will be described in greater detail below.

Figure 8:
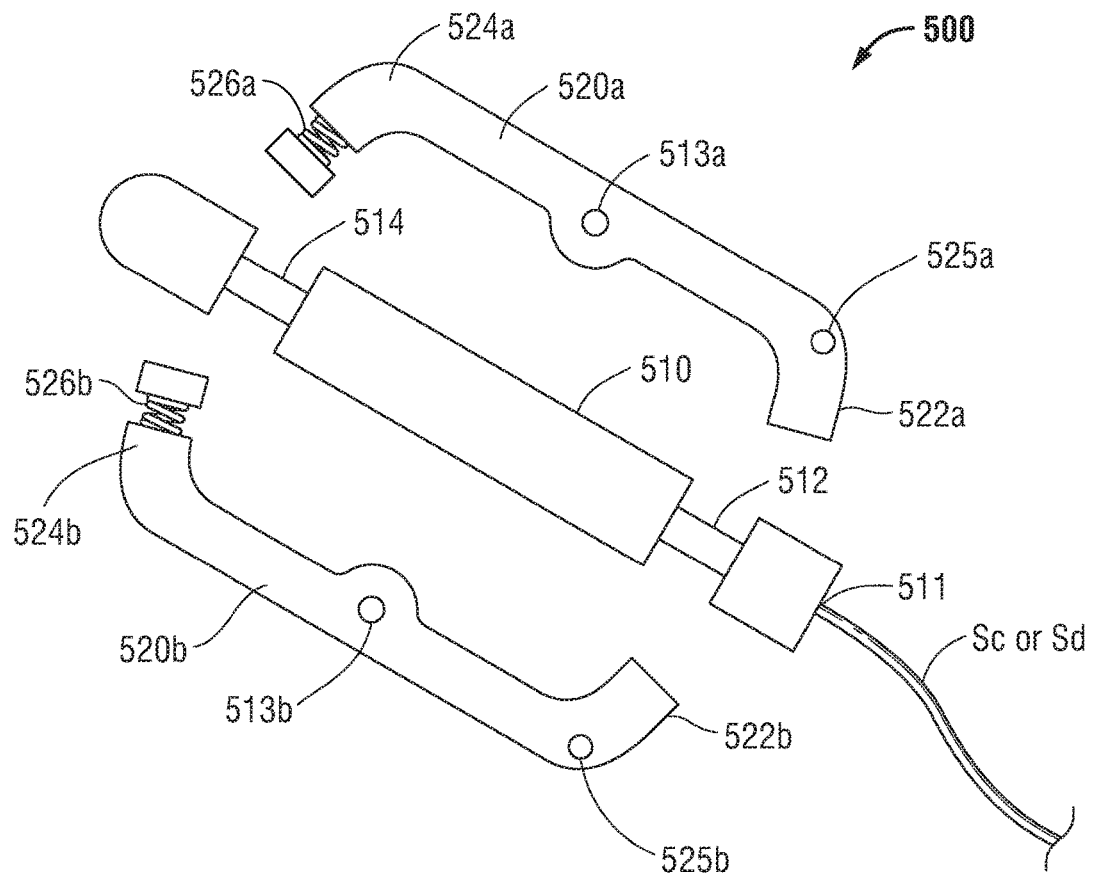
FIG. 8 is a side view of a lower assembly, with parts separated, of the surgical suturing instrument shown in FIG. 1.

Referring also to FIG. 8, lower assembly 500 includes a ferrule 510 and lower bellcranks 520a, 520b. In embodiments, two lower assemblies 500 are coupled to knife assembly 200 (FIG. 4), each being attached to lower knife flange 220 on opposing sides of blade 215. For simplicity, only a single lower assembly 500 will be described. A suture Sc or Sd is attached to a proximal portion 511 of ferrule 510. Ferrule 510 includes proximal waist 512 and distal waist 514. Each proximal and distal waist 512, 514 has a smaller diameter then the body of ferrule 510. Lower bellcranks 520a, 520b include proximal lips 522a, 522b, respectively, and distal lips 524a, 524b, respectively. Proximal waist 512 is configured to receive the proximal lips 522a, 522b of lower bellcranks 520a, 520b and distal waist 514 is configured to receive distal lips 524a, 524b of lower bellcranks 520a, 520b.

In embodiments, distal lips 524a, 524b include resilient members 526a, 526b. Additionally, lower bellcranks 520a, 520b include cam followers 525a, 525b disposed adjacent proximal ends thereof. Although cam followers 525a, 525b are illustrated and described as being disposed adjacent proximal end of lower bellcranks 520a, 520b, it is contemplated that cam followers 525a, 525b may be disposed on any portion of the lower bellcranks 520a, 520b.

Turning again to FIGS. 4-6, and with continued reference to FIGS. 7 and 8, upper bellcrank 420 is pivotably coupled to the upper knife flange 210 such that upper bellcrank 420 may pivot about pivot 411. As described above, upper bellcrank 420 includes cam followers 412a, 412b and needles 414a, 414b positioned on each side of the upper bellcrank 420. Needles 414a, 414b are pivotally coupled to respective end portions of upper bellcrank 420 about pivot points 413a and 413b, respectively. Cam followers 412a, 412b are configured to move or slide along upper cam surfaces 612a, 612b, respectively. Upper cam surfaces 612a, 612b extend along the length of the upper jaw member 110 and define an undulating, or wavelike (e.g. sinusoidal), surface. As the knife assembly 200 is advanced distally through the end effector 100, cam follower 412a moves or slides along cam surface 612a and cam follower 412b moves or slides along cam surface 612b. The undulating cam surfaces 612a, 612b cause the upper bellcrank 420 to rotate about pivot 411 in reciprocating fashion, as illustrated by arrow "A" (FIG. 4), as the knife assembly 200 is advanced distally through the knife slot 96 of end effector 100. The reciprocating movement of the upper bellcrank 410 about pivot 411 (caused by the interaction between the cam followers 412a, 412b and the undulating upper cam surfaces 612a, 612b) causes needle 414a to move through needle slots 39a, 39c, and 39e, and causes needle 414b to move through needle slots 39b, 39d, and 39f.

As discussed above, needles 414a, 414b include apertures 415a, 415b, respectively, located at distal portions thereof which receive sutures Sa and suture Sb respectively. In an embodiment, sutures Sa, Sb may be a one-way or barbed suture, where the suture includes an elongated body having a plurality of barbs extending therefrom. In such configurations, the barbs are oriented in such a way that the barbs cause the suture Sa, Sb to resist movement in a direction towards the bellcrank 420. Suitable sutures for use with the surgical suturing instrument 10 include, and are not limited to, those sutures described and disclosed in U.S. Pat. No. 8,414,612, the entire content of which is incorporated herein by reference.

Turning now to FIG. 6A, and continuing with reference to FIGS. 4 and 8, lower bellcranks 520a, 520b of lower assembly 500 are pivotally coupled to lower knife flange 220. In particular, one pair of lower bellcranks 520a, 520b of lower assembly 500 is pivotally coupled to lower knife flange 220 on one side of blade 215 and a second pair of lower bellcranks 520a, 520b is operably coupled to lower knife flange 220 on the other side of blade 215. The ferrule 510 is positioned between each pair of lower bellcranks 520a, 520b. For simplicity, only one lower assembly 500 will be described.

Lower bellcranks 520a, 520b are configured to advance ferrule 510 distally through lower jaw member 120 in such a manner that ferrule 510 may pass through a loop L (FIG. 6A) created by suture Sa, thus creating a stitch. To this end, lower bellcranks 520a, 520b are pivotally coupled to lower knife flange 220, such that lower bellcrank 520a may pivot about pivot 513a and lower bellcrank 520b may pivot about pivot 513b. Cam followers 525a, 525b are configured to move or slide along lower cam channels 614a, 614b, respectively, as knife assembly 200 is advanced distally through end effector 100. With particular reference to FIG. 6A, lower cam channels 614a, 614b extend along the length of lower jaw member 120 and define an undulating, or wavelike, surface. As the knife assembly 200 is advanced distally through the end effector 100, cam follower 525a moves or slides along cam channel 614a and cam follower 525b moves or slides along cam channel 614b. The undulating cam channels 614a, 614b cause the lower bellcrank 520a to rotate in reciprocating fashion about pivot 513a and lower bellcrank 520b to rotate in reciprocating fashion about pivot 513b as the knife assembly 200 is advanced distally through the knife slot 96 of end effector 100. The reciprocating movement of the lower bellcranks 520a, 520b about pivots 513a, 513b causes the proximal lips 522a, 522b to move into and out of engagement with the proximal waist 512 of the ferrule 510 and the distal lips 524a, 524b to the distal waist 514 of the ferrule 510, to effect distal advancement of the ferrule 510 and the suture Sc or Sd, attached thereto.

Figure 6B:
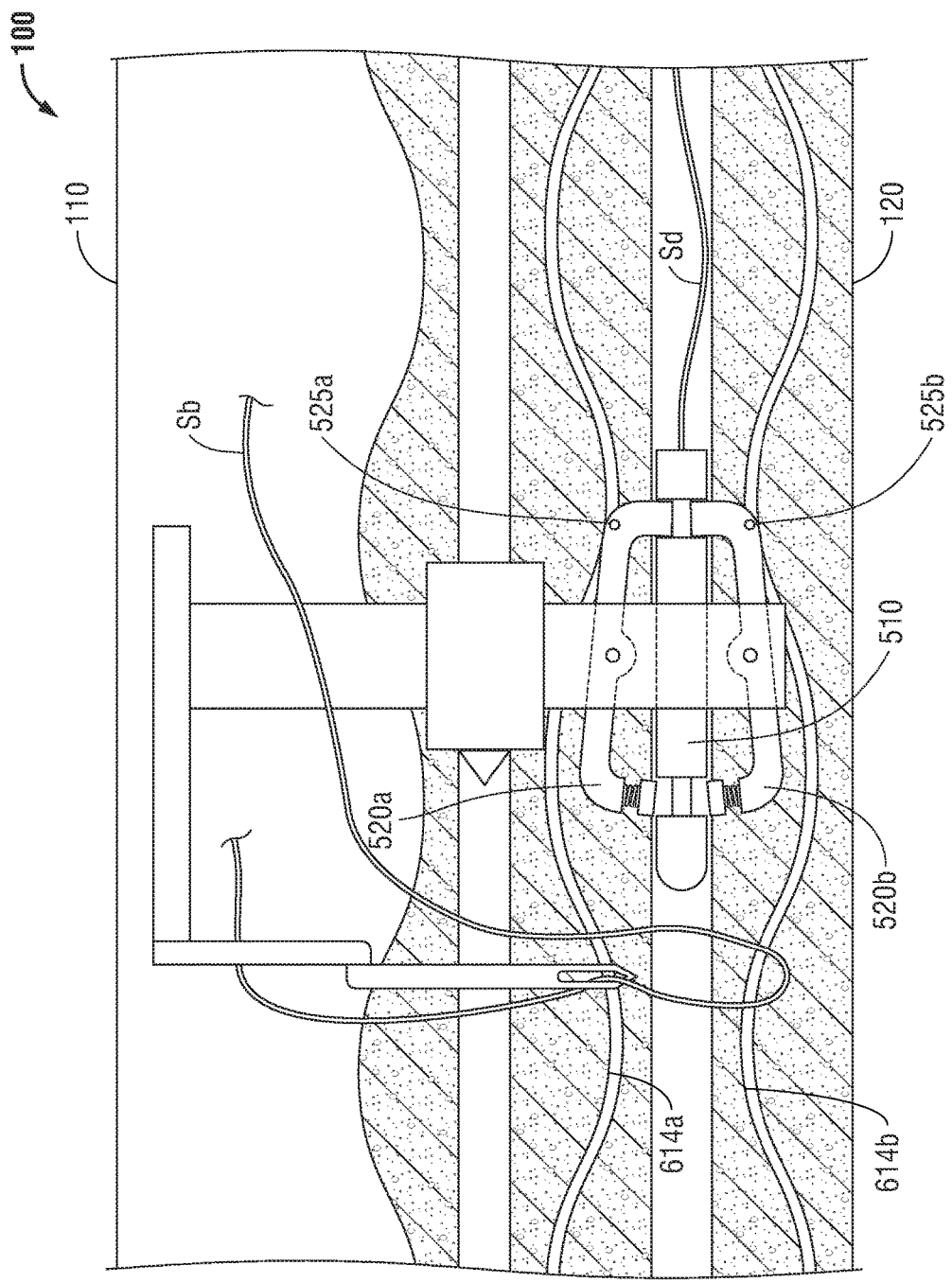
FIG. 6B is a side cross-sectional view of an end effector in accordance with another embodiment of the present disclosure.
Figure 6C:
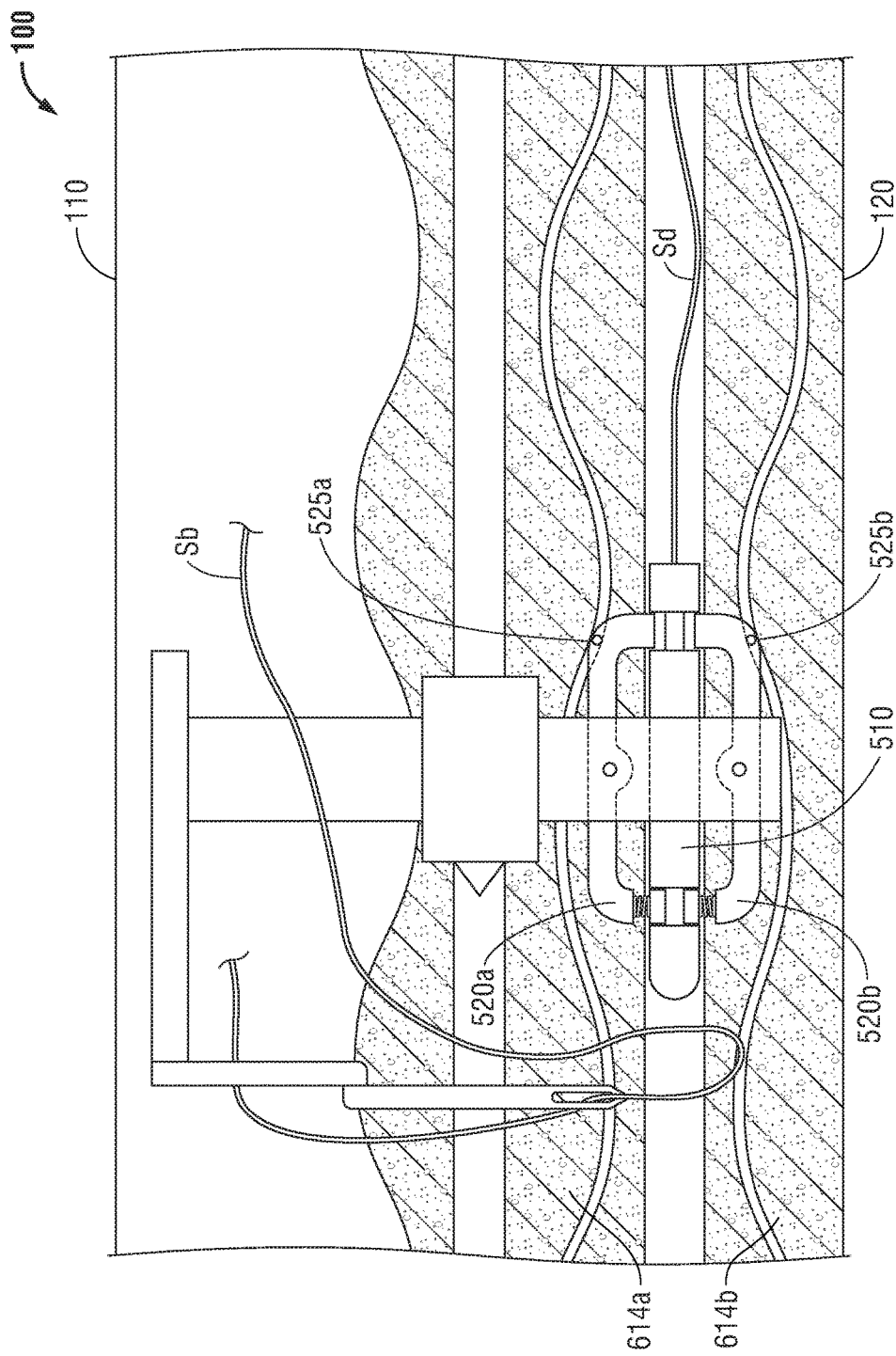
FIG. 6C is a side cross-sectional view of the end effector of FIG. 6B.

FIGS. 6B and 6C illustrate another configuration of lower assembly 500 where second jaw member 120 has a pair of vertically arranged cam channels 614a, 614b. The configuration of FIG. 6B is similar to the configuration of FIG. 6A and therefore only the differences between the two will be described. In FIG. 6B, the lower bellcranks 520a, 520b are pivotally coupled to opposing sides of blade 215, instead of the lower knife flange 220 of FIG. 6A, such that cam followers 525a, 525b may move or slide along the undulating surface of lower cam channels 614a, 614b, respectively, as knife assembly 200 is advanced distally. FIG. 6C illustrates the ferrule 510 in a position with the lower bellcranks 520a, 520b engaging the ferrule 510 to translate the ferrule 510 through the end effector 100.

Figure 9B:
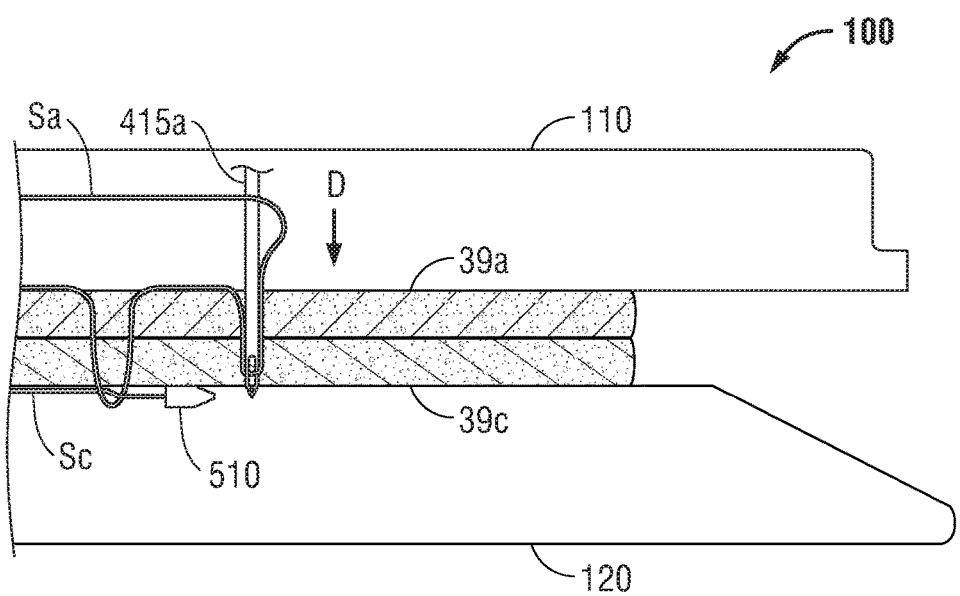
FIG. 9B is a side cross-sectional view of the end effector of FIG. 9A with the needle assembly in a second position.
Figure 9C:
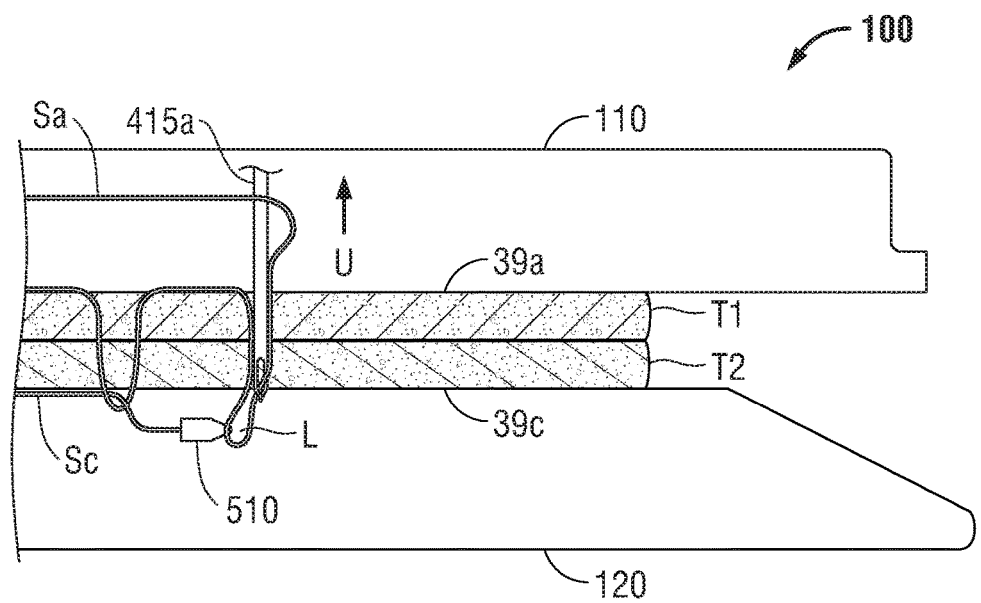
FIG. 9C is a side cross-sectional view of the end effector of FIG. 9A with the needle assembly in a third position.
Figure 9D:
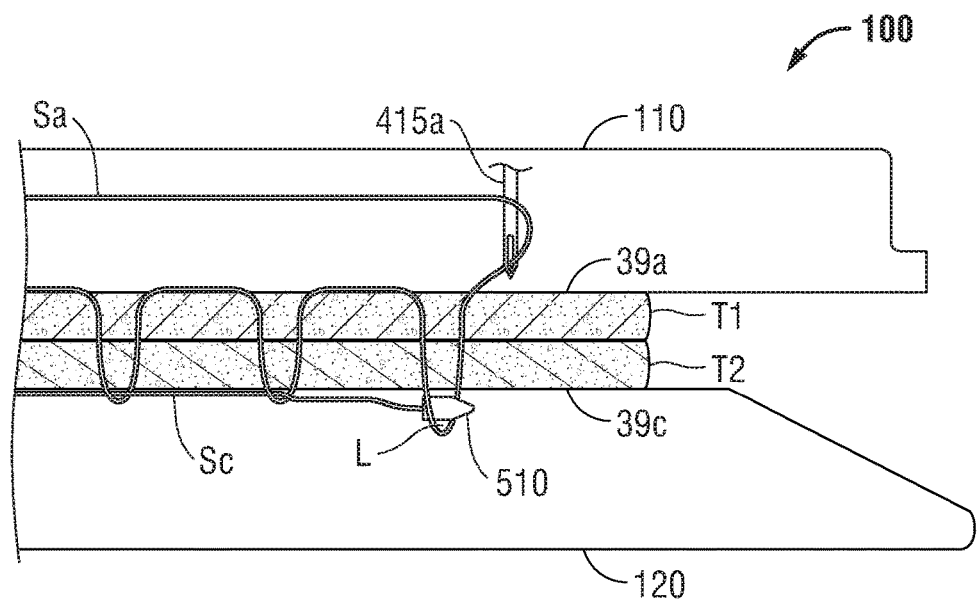
FIG. 9D is a side cross-sectional view of the end effector of FIG. 9A with the needle assembly in a fourth position.

Turning now to FIGS. 9A-9D, use of a surgical suturing instrument 10 for stitching tissue portions will now be described. Upon grasping tissue portions T1 and T2 between jaw members 110, 120, knife assembly 200 is advanced distally through end effector 100. In embodiments, the knife assembly 200 can be advanced through the end effector 100 to move the end effector 100 to a clamped configuration and to suture tissue as disclosed in U.S. Pat. No. 5,865,361 which is incorporated herein by reference. Alternatively, other actuating mechanisms can be used to advance the knife assembly 200 in relation to the end effector 100. As described above, distal advancement of knife assembly 200 through end effector 100 causes reciprocating movement of upper assembly 400 via cam surfaces 612a, 612b, and lower assembly 500 via cam channels 614a, 614b. In particular, as illustrated in FIGS. 9A and 9B, needle 415a is advanced downward, in the direction of arrow D, through needle slot 39a. Once needle 415a protrudes through needle slot 39a, needle 415a pierces through tissue portions T1 and T2 and enters the lower jaw member 120 through needle slot 39c. Further distal advancement of knife assembly 200 then causes needle 415a to move upward, in the direction of arrow U (FIG. 9C), through needle slot 39c, tissue portions T1 and T2, and needle slot 39a. Upon transitioning from the positions shown in FIGS. 9A and 9B to the positions shown in FIGS. 9C and 9D (upon switching from the downward movement direction to the upward movement direction) the suture Sa creates a loop L (FIG. 9C) in the bottom jaw member 120.

After creating loop L, and upon further distal advancement of knife assembly 200 through end effector 100, ferrule 510 is advanced through loop L to create a stitch. Briefly referring back to FIG. 6A, as lower assembly 500 is advanced distally through the lower jaw member 120, lower cam channels 614a, 614b cause the lower bellcranks 520a, 520b to pivot about pivot point 513a, 513b, respectively, such that proximal lips 522a, 522b engage the proximal waist 512 of ferrule 510, leaving the distal end of ferrule 510 open to pass the distal portion of ferrule 510 through loop L created by needle 415a. Once ferrule 510 is passed through loop L, as lower assembly 500 is advanced even further distally through the lower jaw member 120, lower cam channels 614a, 614b cause the lower bellcranks 520a, 520b to pivot about pivot point 513a, 513b, respectively, such that proximal lips 522a, 522b disengage the proximal waist 512 of ferrule 510, and distal lips 524a, 524b engage distal waist 514, leaving the proximal portion 511 of ferrule 510 open to pass loop L through the entire lower assembly 500 and onto suture Sc, thus creating a stitch.

This process is repeated forming additional stitches until the knife assembly 200 reaches the distal end portion of the end effector 100 or until a desired portion of tissue is stitched and cut.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed:
1. A surgical suturing instrument comprising:
a handle assembly;
an elongate member extending distally from the handle assembly, the elongate member defining a longitudinal axis;
an end effector attached to a distal end of the elongate member, the end effector including:
a first jaw member movable relative to a second jaw member between an open position and an approximated position for grasping tissue, each of the first jaw member and the second jaw member defining a knife slot extending along a longitudinal axis of the end effector;

a knife assembly configured to advance through the knife slot, the knife assembly including an upper knife flange, a lower knife flange, and a cutting element between the upper knife flange and the lower knife flange;

an upper bellcrank pivotably coupled to the upper knife flange; and a first needle pivotably coupled to a first end of the upper bellcrank, the first needle defining a first aperture for supporting a first suture therethrough.

2. The surgical instrument according to claim 1, wherein the handle assembly includes a fixed handle and a movable handle, wherein movement of the movable handle toward the fixed handle causes approximation of the first jaw member relative to the second jaw member.

3. The surgical instrument according to claim 1, wherein the handle assembly includes a fixed handle and a movable handle and wherein movement of the movable handle toward the fixed handle causes approximation of the first jaw member relative to the second jaw member and further causes distal advancement of the knife assembly through the end effector.

4. The surgical instrument according to claim 1, wherein the end effector further comprises a second needle pivotably coupled to a second end of the upper bellcrank, the second needle defining a second aperture for supporting a second suture therethrough.

5. The surgical instrument according to claim 1, wherein the end effector further includes:

first and second upper cam surfaces extending along a length of the first jaw member; and first and second cam followers disposed on the upper bellcrank configured to slide along the first upper cam surface and the second upper cam surface.

6. The surgical instrument according to claim 5, wherein the first upper cam surface and the second upper cam surface are undulating surfaces.

7. The surgical instrument according to claim 1, wherein the end effector further includes:

a lower assembly including:

a first lower bellcrank and a second lower bellcrank pivotably coupled to the lower knife flange, each of the first lower bellcrank and the second lower bellcrank having a proximal lip, a distal lip, and a cam follower;

a ferrule having a proximal waist configured to engage the proximal lip of the first lower bellcrank and the proximal lip of the second lower bellcrank, and a distal waist configured to engage the distal lip of the first lower bellcrank and the distal lip of the second lower bellcrank; and a third suture coupled to a proximal portion of the ferrule.

8. The surgical instrument according to claim 7, wherein the end effector further includes first and second lower cam channels extending along a length of the second jaw member, wherein the cam follower of the first lower bellcrank is configured to slide along the first lower cam channel and the cam follower of the second lower bellcrank is configured to slide along the second lower cam channel.

9. The surgical instrument according to claim 1, further comprising a first needle slot and a second needle slot located on opposite sides of the knife slot.

\* \* \* \* \*